United States Patent
Barth et al.

(10) Patent No.: US 6,645,985 B2
(45) Date of Patent: *Nov. 11, 2003

(54) PYRAZOLECARBOXYLIC ACID DERIVATIVES, THEIR PREPARATION AND PHARMACEUTICAL COMPOSITIONS CONTAINING THEM, AND METHOD OF TREATING

(76) Inventors: Francis Barth, 5 allée des Terres Rouges, 34680 Saint Georges d'Orques (FR); Philippe Camus, 111 rue de Guyenne, FR-31600 Muret (FR); Serge Martinez, 4 rue Raoul, FR-34000 Montpellier (FR); Murielle Rinaldi, 2 rue des Fontardies, FR-34080 Saint Georges d'Orques (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/165,140

(22) Filed: Jun. 7, 2002

(65) Prior Publication Data

US 2002/0188007 A1 Dec. 12, 2002

Related U.S. Application Data

(62) Division of application No. 09/890,242, filed as application No. PCT/FR00/00194 on Jan. 28, 2000, now Pat. No. 6,432,984.

(30) Foreign Application Priority Data

Feb. 1, 1999 (FR) .............................................. 99 01201
Aug. 2, 1999 (FR) .............................................. 99 10166

(51) Int. Cl.⁷ ................ A61K 31/4427; A61K 31/4439; C07D 401/12
(52) U.S. Cl. ....................................... 514/326; 546/211
(58) Field of Search ........................... 514/326; 546/211

(56) References Cited

U.S. PATENT DOCUMENTS 5,624,941 A    4/1997   Barth et al. .................. 514/326
6,432,984 B1 * 8/2002   Barth et al. .................. 514/326

FOREIGN PATENT DOCUMENTS

EP    0 576 357    12/1993
EP    0 656 354     6/1995

OTHER PUBLICATIONS

Caplus, English Abstract DN 129:12298, Brian Thomas et al 1998, pp. 285–292.*
Caplus, English Abstract DN 125:321765, Lan Ruoxi et al, 1996, Vol 38, pp. 875–881.*
Preparation of Iodine–123 labeled . . . Ruoxi Ian et al Journal of labelled Compounds and radiopharmaceuticals Vol 38. 1996.*
Comparative receptor Binding Analyses of Cannabinoid agonists and Antagonists 1998, Vol 285, No 1, Brian Thomas et al.*
Chemical Abstract No. 129; 12298 (1998).
Chemical Abstract No. 125; 321765 (1996).
Chemical Abstract No. 123; 286006 (1995).

* cited by examiner

Primary Examiner—Rita Desai

(57) ABSTRACT

N-Piperidino-5-(4-bromophenyl)-1-(2,4-dichlorophenyl)-4-ethylpyrazole-3-carboxamide and its salts and solvates are powerful antagonists of the $CB_1$ cannabinoid receptors. They are prepared by reacting a functional derivative of 5-(4-bromophenyl)-1-(2,4-dichlorophenyl)-4-ethylpyrazole-3-carboxylic acid with 1-aminopiperidine, optionally followed by salification.

2 Claims, No Drawings

PYRAZOLECARBOXYLIC ACID DERIVATIVES, THEIR PREPARATION AND PHARMACEUTICAL COMPOSITIONS CONTAINING THEM, AND METHOD OF TREATING

CROSS REFERENCE TO RELATED APPLICATIONS

This application is a divisional of prior copending application Ser. No. 09/890,242, filed Jul. 27, 2001 now U.S. Pat. No. 6,432,984, which in turn is a 35 U.S.C. §371 application of PCT International application No. PCT/FR00/00194, filed Jan. 28, 2000, which in turn claims priority from French application No. 99/01201, filed Feb. 1, 1999 and French application No. 99/110166, filed Aug. 2, 1999.

The present invention relates to a novel pyrazole derivative, to its salts and to the solvates thereof, to a process for their preparation and to pharmaceutical compositions containing them.

Patent applications EP-A-576 357, EP-A-658 546 and WO-97/19063 describe pyrazole derivatives with affinity for cannabinoid receptors. More particularly, patent application EP-A-656 354 describes N-piperidino-5-(4-chlorophenyl)-1-(2,4-dichlorophenyl)-4-methylpyrazole-3-carboxamide, also known as SR 141 716, and the pharmaceutically acceptable salts thereof which have very good affinity for the central cannabinoid receptors.

Compounds similar to SR 141716 have been described in the literature, in particular N-piperidino-5-(4-bromophenyl)-1-(2,4-dichlorophenyl)-4-methylpyrazole-3-carboxamide, referred to hereinbelow as compound A, which is described by B. F. Thomas et al. in J. Pharm. Exp. Therap., 1998, 285, 285–292.

The effects of cannabinoids are due to an interaction with specific high-affinity receptors present at the central level (Devane et al., Mol. Pharmacol., 1988, 34, 605–613) and at the peripheral level (Nye et al., Pharmacol. and Experimental Ther., 1985, 234, 784–791; Kaminski et al., 1992, Mol. Pharmacol., 42, 736–742; Munro et al., Nature, 1993, 365, 61–65).

Characterization of the receptors was made possible by the development of synthetic ligands specific for cannabinoid receptors, such as the agonist WIN 55212-2 (J. Pharmacol. Exp. Ther., 1993, 264, 1352–1363) or CP 55,940 (J. Pharmacol. Exp. Ther., 1988, 247, 1046–1051). The pharmacology of the $CB_1$ and $CB_2$ cannabinoid receptor subtypes is outlined in Pharmacol. Ther., 1997, 74, 129–130.

A novel N-piperidino-3-pyrazolecarboxamide derivative has now been found which has very good affinity for the $CB_1$ subtype of cannabinoid receptors ($CB_1$ receptors) with long-lasting action, which is useful in the therapeutic fields in which cannabinoids are known to be involved.

According to one of its aspects, the present invention relates to N-piperidino-5-(4-bromophenyl)-1-(2,4-dichlorophenyl)-4-ethylpyrazole-3-carboxamide, of formula:

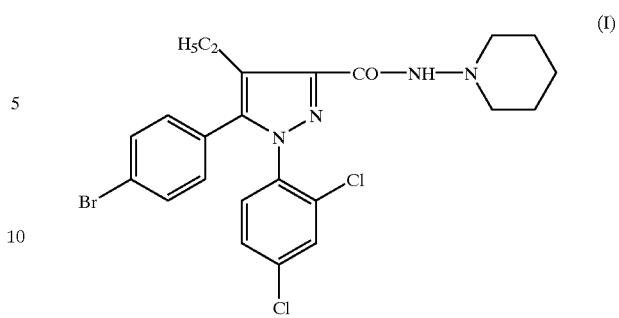

to its pharmaceutically acceptable salts and to the solvates thereof.

According to another of its aspects, the present invention relates to a process for preparing compound (I) above, its salts and the solvates thereof, characterized in that a functional derivative of 5-(4-bromophenyl)-1-(2,4-dichlorophenyl)-4-ethylpyrazole-3-carboxylic acid, of formula:

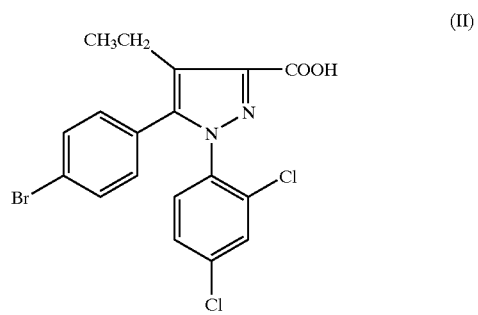

is treated with 1-aminopiperidine, in an organic solvent and in the presence of a base; and the compound thus obtained is optionally converted into one of its salts or one of the solvates thereof.

The reaction is carried out in basic medium, for example in the presence of triethylamine in an inert solvent such as dichloromethane or tetrahydrofuran.

Functional derivatives of the acid (II) which may be used are the acid chloride, the anhydride, a mixed anhydride, a $C_1$–$C_4$ alkyl ester in which the alkyl is straight or branched, an activated ester, for example the p-nitrophenyl ester, or the suitably activated free acid, for example activated with N,N-dicyclohexylcarbodiimide or with benzotriazole-N-oxotris(dimethylamino)phosphonium (BOP) hexafluorophosphate.

Thus, by means of the process according to the invention, it is possible to react the acid chloride of formula (II) obtained by reacting thionyl chloride with the acid of formula (II) in an inert solvent, such as benzene or toluene, or a chlorinated solvent (for example dichloromethane, dichloroethane or chloroform), an ether (for example tetrahydrofuran or dioxane), or an amide (for example N,N-dimethylformamide) under an inert atmosphere, at a temperature of between 0° C. and the reflux point of the solvent.

One variant of the procedure consists in preparing the mixed anhydride of the acid of formula (II) by reacting ethyl chloroformate with the acid of formula (II), in the presence of a base such as triethylamine.

The acid of formula (II) can be prepared according to the reaction scheme described below, in which:
LiHMDS=lithium hexamethyldisilazide
NBS=N-bromosuccinimide.

SCHEME 1

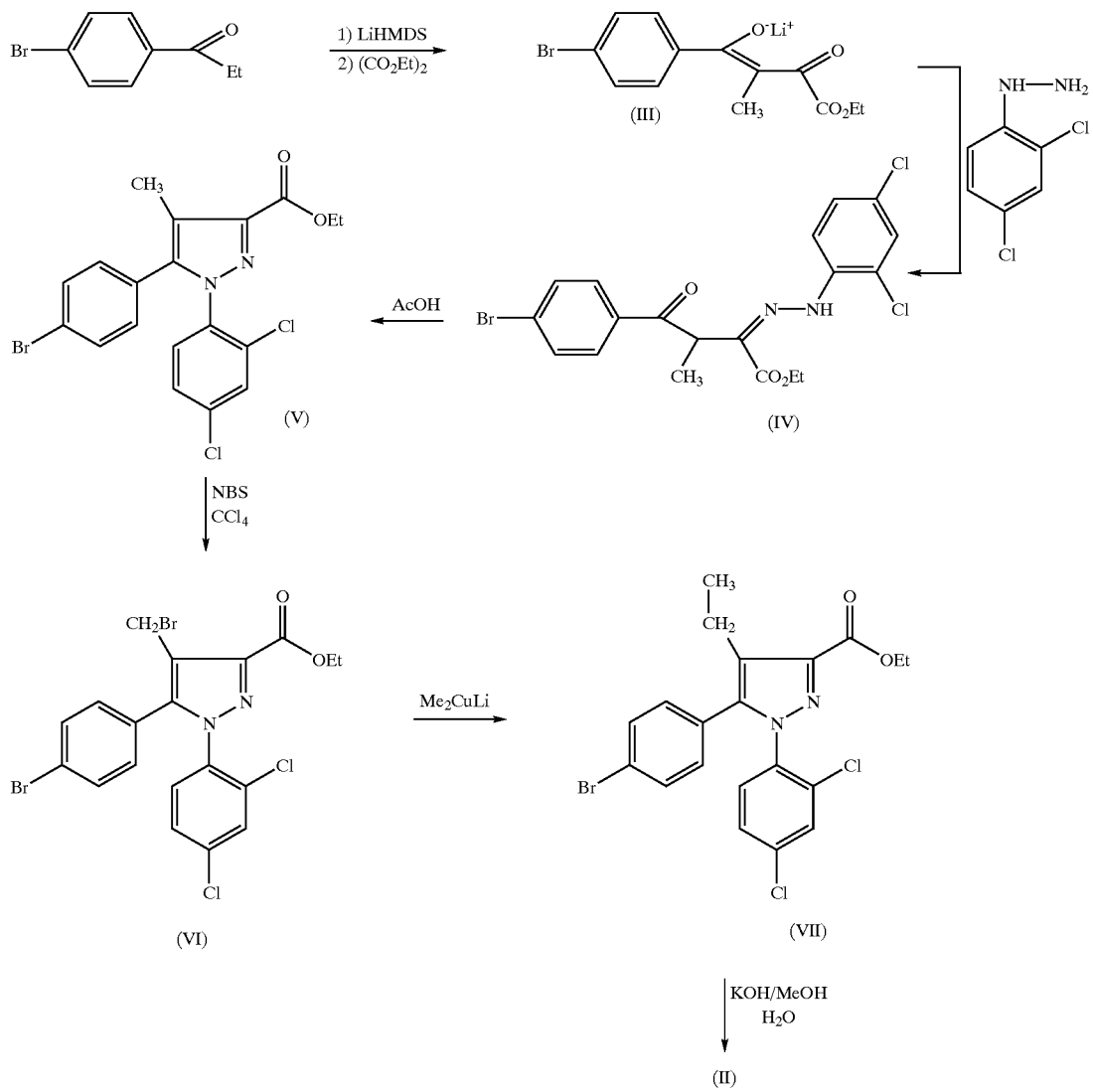

The first step is carried out according to J. Heterocyclic. Chem., 1989, 26, 1389. In the penultimate step, the conversion of the 4-bromomethyl substituent of the pyrazole into 4-ethyl is carried out according to J. Am. Chem. Soc., 1968, 90, 5615.

The 1-aminopiperidine used is a commercial product.

The ester of formula (VII) and the acid of formula (II) can be prepared according to another process which constitutes a further subject of the present invention.

This process is illustrated by the reaction scheme below, in which Alk represents a $(C_1-C_6)$alkyl and represents an ethyl.

SCHEME 2

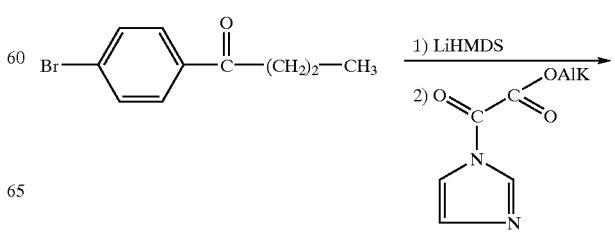

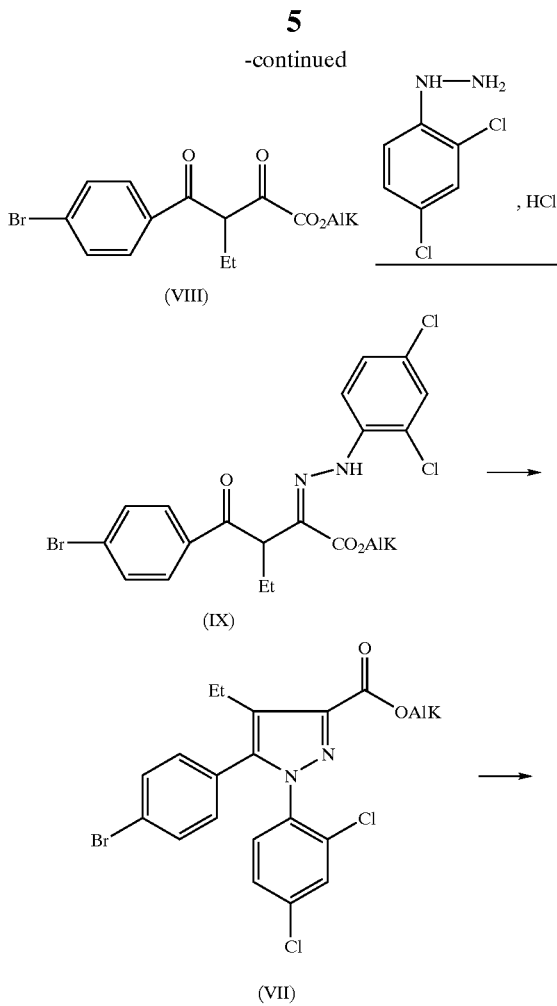

(VIII)

(IX)

(VII)

This process is characterized in that an alkyl ester, preferably the ethyl ester, of 5-(4-bromophenyl)-1-(2,4-dichlorophenyl)-4-ethylpyrazole-3-carboxylic acid is prepared by cyclization of an alkyl ester, preferably the ethyl ester, of 3-(4-bromobenzoyl)-2-(2-(2,4-dichlorophenyl) hydrazono)pentanoic acid (IX).

This reaction is carried out in a protic solvent such as an alcohol, for example a $C_1$–$C_4$ alcohol, preferably ethanol, at a temperature of between room temperature and 80° C., preferably in refluxing ethanol.

According to the invention, the alkyl ester, preferably the ethyl ester, of 3-(4-bromobenzoyl)-2-(2-(2,4-dichlorophenyl)hydrazono)pentanoic acid is prepared by the action of a 2,4-dichlorophenylhydrazine salt, preferably the hydrochloride, on an alkyl ester, preferably the ethyl ester, of 4-bromobenzoyl-2-oxopentanoic acid (VIII).

The reaction is carried out in a protic solvent, for example a $C_1$–$C_4$ alcohol, preferably ethanol.

According to the invention, the alkyl ester, preferably the ethyl ester, of 4-bromobenzoyl-2-oxopentanoic acid is prepared by the action of LiHMDS and then of an alkyl ester, preferably the ethyl ester, of 2-(1-imidazolyl)-2-oxoacetic acid on bromobutyrophenone.

The reaction is carried out in an organic solvent such as an aromatic solvent or an ether, preferably methyl tert-butyl ether. The first step of this reaction is carried out at low temperature, for example at a temperature between 0° C. and −60° C., preferably at a temperature in the region of −20° C.; the second step is carried out at a temperature of between room temperature and −20° C., preferably at room temperature.

Thus, according to Scheme 2, the preparation of an alkyl ester of 5-(4-bromophenyl)-1-(2,4-dichlorophenyl)-4-ethylpyrazole-3-carboxylic acid (VII) is carried out starting with 4-bromobenzoyl-2-oxopentanoic acid (VIII) by the action of a 2,4-dichlorophenylhydrazine salt, followed by cyclization.

Bromobutyrophenone is commercially available.

The ethyl ester of 2-(1-imidazolyl)-2-oxoacetic acid is described and prepared according to J. Org. Chem., 1981, 46 (1), 211–213.

The present invention also comprises a process for preparing an alkyl ester, preferably the ethyl ester, of 5-(4-bromophenyl)-1-(2,4-dichlorophenyl)-4-ethylpyrazole-3-carboxylic acid, from 4-bromobenzoyl-2-oxopentanoic acid, by the action of a 2,4-dichlorophenylhydrazine salt, preferably the hydrochloride, in a protic solvent, for example a $C_1$–$C_4$ alcohol, preferably ethanol. The reaction is carried out at a temperature of between room temperature and 80° C., preferably in refluxing ethanol.

The compounds of formula:

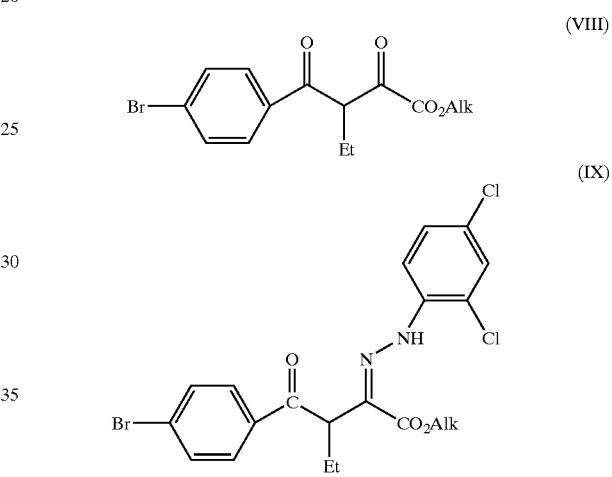

in which Alk represents a $(C_1$–$C_6)$alkyl are novel and form part of the invention. Preferably, Alk represents an ethyl.

The compound of formula (I) obtained by the process according to the invention is isolated, in the form of the free base or of a salt or solvate, according to the conventional techniques.

The pharmaceutically acceptable salts of the compound of formula (I) comprise the addition salts with acids, such as the hydrochloride, the hydrobromide, the sulphate, the hydrogen sulphate, the dihydrogen phosphate, the methanesulphonate, the methyl sulphate, the oxalate, the maleate, the fumarate, the 2-naphthalenesulphonate, the glyconate, the gluconate, the citrate, the isethionate, the para-toluenesulphonate or the succinate.

The compound of formula (I) can be isolated in the form of one of its salts, for example the hydrochloride or the oxalate; in this case, the free base can be prepared by neutralizing the said salt with an inorganic or organic base, such as sodium hydroxide or ammonium hydroxide, triethylamine or an alkali metal carbonate or bicarbonate such as sodium or potassium carbonate or bicarbonate, and converted into another salt such as the methanesulphonate, fumarate or 2-naphthalenesulphonate.

When the compound of formula (I) is obtained in the form of the free base, the salification is carried out by treatment with the acid chosen in an organic solvent. By treating the free base, dissolved, for example, in an ether such as diethyl ether or in acetone, with a solution of the acid in the same solvent, the corresponding salt is obtained and is then isolated according to the conventional techniques.

The compounds of formula (I) have very good in vitro affinity for the $CB_1$ cannabinoid receptors, under the experimental conditions described by Devane et al., Mol. Pharmacol., 1988, 34, 605–613.

Thus, the compound according to the invention has very strong affinity for human $CB_1$ cannabinoid receptors (Ki= 5.4 nM) which compares favourably with that of SR 141716 for the same receptors, determined under the same conditions (Ki=34 nM).

The compound according to the invention was also compared with N-piperidino-5-(4-bromophenyl)-1-(2,4-dichlorophenyl)-4-methylpyrazole-3-carboxamide, (compound A). The affinity of this compound for human $CB_1$ cannabinoid receptors, measured under the same conditions, is reflected by a Ki value of 8 nM.

Moreover, the duration of occupation of the $CB_1$ receptors present in the brain by the 3 compounds below was compared:

the compound of formula (I) according to the invention,

SR 141716, compound A.

The study was performed in vivo in mice, after oral administration of each of the compounds at a dose of 10 mg/kg, according to the technique described in M. Rinaldi-Carmona et al., Life Sciences, 1995, 56, 1941–1947. The results obtained are collated in the table below:

TABLE 1

|  | % of occupation of the receptors | |
| --- | --- | --- |
|  | 1 hour | 24 hours |
| Compound of formula (I) | 82% | 44% |
| SR 141716 | 69% | 4% |
| Compound A | 89% | 4% |

Surprisingly, it is observed that the compound of formula (I) according to the invention is the only compound which shows appreciable occupation (44%) 24 hours after its administration.

Moreover, the antagonist nature of the compound of formula (I) was demonstrated by the results obtained in models of adenylate-cyclase inhibition as described in M. Rinaldi-Carmona et al., J. Pharmacol. Exp. Ther., 1996, 278, 871–878.

More particularly, the compound of the present invention, in its native form or in the form of one of its pharmaceutically acceptable salts, is a powerful and selective antagonist of the $CB_1$ cannabinoid receptors.

The antagonist nature of the compound according to the invention, as well as its good penetration into the central nervous system, are confirmed by the results obtained in the model of antagonism of the hypothermia induced with a cannabinoid receptor agonist. Thus, the compound of formula (I) according to the invention antagonizes the hypothermia induced with WIN 55212-2 in mice, with an oral $ED_{50}$ of 0.3 mg/kg in the test described by Pertwee R. G. et al. in Marijuana, 84, Ed. Harvey, D. Y. Oxford IRL Press, 1985, 263–277. In this test, the activity and the duration of action of 3 compounds were compared. The results obtained are collated in the table below:

TABLE 2

Antagonism of the hypothermia induced

|  |  | Duration of action | |
| --- | --- | --- | --- |
|  | oral $ED_{50}$ | oral dose | 24 h |
| Compound of formula (I) | 0.3 mg/kg | 1 mg/kg | active |
| SR 141716 | 0.4 mg/kg | 1 mg/kg | not active |
|  |  | 10 mg/kg | active |
| Compound A | 0.3 mg/kg | 1 mg/kg | not active |
|  |  | 10 mg/kg | active |

It is found that the compound of the present invention has an $ED_{50}$ which is comparable with those of the compounds of the prior art, but its duration of action is markedly longer.

Thus, whereas 24 hours after their administration, SR 141716 and compound A are only active at a dose of 10 mg/kg/p.o., the compound of formula (I) according to the invention is active 24 hours after its administration, at a dose 10 times lower (1 mg/kg/p.o.).

The long-lasting action of the compound of formula (I) according to the invention is particularly noteworthy and represents an important advantage for its use as a medicinal product.

The toxicity of compounds (I) is compatible with their use as medicinal products.

According to another of its aspects, the present invention relates to the use of a compound of formula (I), or one of the pharmaceutically acceptable salts or solvates thereof, for the preparation of medicinal products intended for treating diseases involving the $CB_1$ cannabinoid receptors.

For example, and in a non-limiting manner, the compound of formula (I) is useful as a psychotropic medicinal product, in particular for the treatment of anxiety disorders, mood disorders, delirium disorders, psychotic disorders in general, for the treatment of schizophrenia and depression, as well as for the treatment of disorders associated with the use of psychotropic substances, in particular in the case of abuse of a substance and/or dependence on a substance, including alcohol dependency and nicotine dependency.

The compound of formula (I) according to the invention can be used as medicinal product for treating neuropathies, migraine, stress, diseases of psychosomatic origin, epilepsy, locomotor disorders, in particular dyskinesias or Parkinson's disease.

The compound of formula (I) according to the invention can also be used as a medicinal product in the treatment of memory disorders, cognitive disorders, in particular in the treatment of senile dementia and Alzheimer's disease, as well as in the treatment of attention disorders or vigilance disorders. Furthermore, the compound of formula (I) may be useful as a neuroprotective agent, in the treatment of neurodegenerative diseases.

The compound of formula (I) according to the invention can be used as a medicinal product in the treatment of appetite disorders, cravings (for sugars, carbohydrates, drugs, alcohol or any appetizing substance) and/or eating disorders, in particular as an anorexigenic agent or for the treatment of obesity or bulimia, as well as for the treatment of type II diabetes or non-insulin-dependent diabetes. Furthermore, the compound of formula (I) according to the invention can be used as a medicinal product in the treatment of gastrointestinal disorders, diarrheic disorders, ulcers, vomiting, urinary and bladder disorders, cardiovascular disorders, fertility disorders, inflammatory phenomena, infectious diseases and as a medicinal product for anticancer chemotherapy.

According to the present invention, the compound of formula (I) is most particularly useful for treating psychotic disorders, in particular schizophrenia; for treating appetite disorders and obesity, for treating for memory and cognitive disorders; for treating alcohol dependency or nicotine dependency, i.e. for withdrawal from alcohol and for withdrawal from tobacco.

According to one of its aspects, the present invention relates to the use of a compound of formula (I), its pharmaceutically acceptable salts and the solvates thereof for the treatment of the disorders and diseases indicated above.

According to another of its aspects, the present invention also relates to the use of the compounds of formula (I), in their native form or in radiolabelled form, as a pharmacological tool in man or animals, for detecting and labelling the $CB_1$ receptors.

The compound according to the invention is generally administered as a dosage unit.

The said dosage units are preferably formulated in pharmaceutical compositions in which the active principle is mixed with a pharmaceutical excipient.

Thus, according to another of its aspects, the present invention relates to pharmaceutical compositions containing, as active principle, a compound of formula (I), one of its pharmaceutically acceptable salts or a solvate thereof.

The compound of formula (I) above and its pharmaceutically acceptable salts or solvates can be used at daily doses of from 0.01 to 100 mg per kg of body weight of the mammal to be treated, preferably at daily doses of from 0.02 to 50 mg/kg. In human beings, the dose can preferably range from 0.05 to 4000 mg per day, more particularly from 0.1 to 1000 mg per day depending on the age of the individual to be treated or the type of treatment, i.e. prophylactic or curative treatment. Although these doses are examples of average situations, it is possible to have special cases in which higher doses or lower doses are suitable, and such doses also belong to the invention. According to the usual practice, the dose which is suitable for each patient is determined by the doctor according to the method of administration and the age, weight and response of the said patient.

In the pharmaceutical compositions of the present invention for oral, sublingual, inhaled, subcutaneous, intramuscular, intravenous, transdermal, local or rectal administration, the active principle can be administered in unit administration form, as a mixture with conventional pharmaceutical supports, to animals and to human beings. The appropriate unit forms of administration comprise oral-route forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

In the pharmaceutical compositions of the present invention, the active principle is generally formulated in dosage units containing from 0.05 to 1000 mg, advantageously from 0.1 to 500 mg and preferably from 1 to 200 mg, of the said active principle per dosage unit for daily administrations.

When a solid composition is prepared in tablet form, a wetting agent such as sodium lauryl sulphate can be added to the micronized or non-micronized active principle, and the whole is mixed with a pharmaceutical vehicle such as silica, gelatin, starch, lactose, magnesium stearate, talc, gum arabic or the like. The tablets can be coated with sucrose, various polymers or other suitable materials or alternatively they can be treated such that they have sustained or delayed activity and such that they release a predetermined amount of active principle continuously.

A preparation in gel capsule form is obtained by mixing the active principle with a diluent such as a glycol or a glycerol ester and by incorporating the mixture obtained into soft or hard gel capsules.

A preparation in the form of a syrup or elixir can contain the active principle together with a sweetener, preferably a calorie-free sweetener, methyl paraben and propyl paraben as antiseptic agents, as well as a flavour enhancer and a suitable colorant.

The water-dispersible powders or granules can contain the active principle as a mixture with dispersants, wetting agents or suspending agents, such as polyvinylpyrrolidine, as well as with sweeteners or flavour enhancers.

For rectal administration, use is made of suppositories which are prepared with binders that melt at the rectal temperature, for example cocoa butter or polyethylene glycols.

For parenteral, intranasal or intraocular administration, aqueous suspensions, isotonic saline solutions or sterile, injectable solutions which contain pharmacologically compatible dispersants and/or solubilizing agents, for example propylene glycol or polyethylene glycol, are used.

Thus, to prepare an aqueous solution which can be injected intravenously, a co-solvent such as, for example, an alcohol, for instance ethanol or a glycol such as polyethylene glycol or propylene glycol, and a hydrophilic surfactant such as Tween® 80, can be used. To prepare an oily solution which can be injected intramuscularly, the active principle can be dissolved with a triglyceride or a glycerol ester.

Creams, ointments or gels can be used for local administration.

For transdermal administration, patches in multilayer form or containing a reservoir in which the active principle may be in alcoholic solution can be used.

For administration by inhalation, an aerosol is used containing, for example, sorbitan trioleate or oleic acid as well as trichlorofluoromethane, dichlorofluoromethane, dichlorotetrafluoroethane or any other biologically compatible propellent gas; it is also possible to use a system containing the active principle alone or combined with an excipient, in powder form.

The active principle can also be formulated in the form of microcapsules or microspheres, optionally with one or more supports or additives.

The active principle can also be in the form of a complex with a cyclodextrin, for example α-, β- or γ-cyclodextrin, 2-hydroxypropyl-β-cyclodextrin or methyl-β-cyclodextrin.

Among the forms for sustained release which are useful in the case of chronic treatments, it is possible to use implants. These can be prepared in the form of an oily suspension or in the form of a suspension of microspheres in an isotonic medium.

The pharmaceutical compositions of the present invention can contain, along with the compound of formula (I) or one of its pharmaceutically acceptable salts or solvates, other active principles which can be useful in the treatment of the disorders or diseases indicated above.

In the present description, the following abbreviations are used:
DCM: dichloromethane
LiHMDS: lithium hexamethyldisilazide
TMSCl: chlorotrimethylsilane
PTSA: para-toluenesulphonic acid
NBS: N-bromosuccinimide MTBE: methyl tert-butyl ether
RT: room temperature
m.p.: melting point
TLC: thin layer chromatography
NMR: nuclear magnetic resonance. The NMR spectra are recorded at 200 MHz in DMSO-$d_6$
s: singlet; d: doublet; t: triplet; q: quadruplet;
m: broad peak or multiplet; dd: doubled doublet.

Preparation 1

Ethyl 5-(4-bromophenyl)-1-(2,4-dichlorophenyl)-4-ethylpyrazole-3-carboxylate

A) Lithium ethyl 4-(4-bromophenyl)-3-methyl-4-oxido-2-oxobutenoate 21.6 g of LiHMDS are placed in 340 ml of anhydrous ether under nitrogen and the solution is cooled to −60° C., followed by addition of 4 g of bromopropiophenone dissolved in 150 ml of anhydrous ether. This mixture is allowed to warm to −30° C. and 17.53 ml of ethyl oxalate are then added. After stirring overnight at RT, the precipitate formed is filtered off and then rinsed with ether and dried under vacuum. 21.8 g of the expected compound are obtained.

B) Ethyl 4-(4-bromophenyl)-2-[(2,4-dichlorophenyl)-hydrazono]-3-methyl-4-oxobutyrate 16.8 g of the compound prepared in the above step and 12.5 g of 2,4-dichlorophenylhydrazine hydrochloride in 150 ml of ethanol are mixed together and left stirring for 2 and a half hours. The precipitate formed is filtered off, rinsed with ethanol and then dried under vacuum. 16.24 g of the expected compound are obtained.

C) Ethyl 5-(4-bromophenyl)-1-(2,4-dichlorophenyl)-4-methylpyrazole-3-carboxylate 16.24 g of the compound obtained in the above step are heated for 24 hours in 200 ml of acetic acid and the reaction medium is then poured into 1 liter of ice-cold water; the precipitate formed is filtered off, rinsed with water and dried under vacuum. 12.8 g of the expected compound are obtained, and this product is recrystallized from methylcyclohexane, m.p.=133° C.

D) Ethyl 4-bromomethyl-5-(4-bromophenyl)-1-(2,4-dichlorophenyl)pyrazole-3-carboxylate 12.8 g of the ester obtained in the above step are placed in 130 ml of carbon tetrachloride and 5.27 g of N-bromosuccinimide are added, followed by 24 mg of benzoyl peroxide. The mixture is refluxed for 4 hours and is then filtered and concentrated under vacuum. The residue is chromatographed on silica, eluting with a toluene/ethyl acetate mixture (97/3; v/v). 7.24 g of the expected compound are obtained, m.p.=116° C.

E) Ethyl 5-(4-bromophenyl)-1-(2,4-dichlorophenyl)-4-ethylpyrazole-3-carboxylate 2.26 g of CuBr are introduced as a suspension in 100 ml of ether, under argon, followed by dropwise addition at −20° C. of a solution containing 20 ml of 1.6 M methyllithium in ether diluted in 20 ml of ether. After stirring for 10 minutes at −20° C., the suspension decolorizes and then becomes clear. The resulting mixture is cooled to −78° C. and 7 g of the compound prepared in the above step are added as a solution in 100 ml of ether, over 30 minutes, after which the mixture is allowed to warm to RT. After stirring for 2 hours, the mixture is hydrolysed by addition of saturated ammonium chloride solution. The resulting mixture is extracted with ether and washed with water, and then with saturated NaCl solution This solution is dried over $MgSO_4$ and then evaporated to dryness. The residue is chromatographed on silica, eluting with a toluene/ethyl acetate mixture (96/4; v/v). 3.7 g of the expected compound are obtained, m.p.=108° C.

NMR: 1.05 ppm: t: 3H; 1.30 ppm: t: 3H; 2.60 ppm: q: 2H; 4.30 ppm: q: 2H; 7.15 ppm: d: 2H; 7.50–7.75 ppm: m: 5H.

Preparation 2

5-(4-Bromophenyl)-1-(2,4-dichlorophenyl)-4-ethylpyrazole-3-carboxylic Acid (II).

3.6 g of the ester obtained in Preparation 1 are placed in 54 ml of MeOH and a solution containing 1.08 g of KOH in 6.85 ml of water is added. The reaction medium is refluxed for 3 hours and then concentrated under vacuum. The residue is taken up in ice-cold water, acidified to pH=1 with 1 N HCl and then extracted with DCM. 3.3 g of the expected compound are obtained, m.p.=218° C.

NMR: 1.10 ppm: t: 3H; 2.70 ppm: q: 2H; 7.25 ppm: d: 2H; 7.60–7.85 ppm: m: 5H.

Preparation 3

Ethyl 3-(4-bromobenzoyl)-2-oxopentanoate

A solution of 247 g of 4-bromobutyrophenone in 1500 ml of MTBE is added to a solution of 210 g of LiHMDS in 2500 ml of MTBE, while keeping the temperature at −20° C. After stirring for 3 hours at this temperature, 210 g of ethyl 2-(1-imidazolyl)-2-oxoacetate in 1000 ml of MTBE are added over 1 hour, at 10° C., and the mixture is left stirring for 18 hours at room temperature. The lithium salt formed is filtered off and then suspended in 800 ml of MTBE. 800 ml of 6 N hydrochloric acid are added to the suspension. After separation of the phases by settling, the ether phase is washed 4 times with 1000 ml of water and then concentrated under reduced pressure. The expected compound is isolated (263 g). From the NMR analysis, it is a mixture containing 8% of the 4-bromobutyrophenone starting material.

NMR: 0.86 ppm: t: 3H; 1.10 ppm: t: 3H; 1.83 ppm: mt: 2H; 4.15 ppm: q: 2H; 5.19 ppm: t: 1H; 7.70 ppm: d: 2H; 7.98 ppm: d: 2H.

Preparation 4

Ethyl 5-(4-bromophenyl)-1-(2,4-dichlorophenyl)-4-ethylpyrazole-3-carboxylate

A) Ethyl 3-(4-bromobenzoyl)-2-(2-(2,4-dichlorophenyl)-hydrazono)pentanoate

A suspension of 155 g of 2,4-dichlorophenylhydrazine hydrochloride in 1200 ml of ethanol is prepared and 263 g of the compound of Preparation 3 in 1000 ml of ethanol are added at room temperature.

A small portion of the intermediate formed can be isolated by filtration and characterized.

NMR: 0.92 ppm: t: 3H; 1.04 ppm: t: 3H; 1.89 ppm: mt: 2H; 4.16 ppm: q: 2H; 4.76 ppm: t: 1H; 7.42 ppm: mt: 2H; 7.60 ppm: s: 1H; 7.75 ppm: d: 2H; 7.93 ppm: d: 2H; 12.31 ppm: s: 1H.

B) Ethyl 5-(4-bromophenyl)-1-(2,4-dichlorophenyl)-4-ethylpyrazole-3-carboxylate

The suspension obtained is refluxed for 4 hours and then left stirring for 18 hours at room temperature. The product formed is filtered off and then dried under vacuum at 50° C. to give the expected compound (247 g), m.p.=108° C.

NMR: 1.07 ppm: t: 3H; 1.28 ppm: t: 3H; 2.58 ppm: q: 2H; 4.32 ppm: q: 2H; 7.16 ppm: d: 2H; 7.53 ppm: dd: 1H; 7.59 ppm: d: 2H; 7.73 ppm: d+small d: 2H.

EXAMPLE 1

N-Piperidino-5-(4-bromophenyl)-1-(2,4-dichlorophenyl)-4-ethylpyrazole-3-carboxamide A) 5-(4-Bromophenyl)-1-(2,4-dichlorophenyl)-4-ethylpyrazole-3-carboxylic acid chloride 3.2 g of the acid obtained in the above step are placed in suspension in 32 ml of toluene, 1.6 ml of thionyl chloride are added and the mixture is then refluxed for 3 hours. The reaction medium is concentrated under vacuum and then taken up in toluene. The operation is repeated several times. 3.3 g of the expected compound are obtained.

B) N-Piperidino-5-(4-bromophenyl)-1-(2,4-dichlorophenyl)-4-ethylpyrazole-3-carboxamide A solution of 0.23 ml of N-aminopiperidine and 0.29 ml of triethylamine in 20 ml of DCM is prepared, under nitrogen, and is cooled to a temperature of between 0° C. and 5° C. 0.8 g of the acid chloride obtained in the above step in 20 ml of DCM is added. After leaving overnight at RT, the resulting mixture is poured onto ice-cold water and the phases are separated by settling. The organic phase is extracted with DCM and then washed with water, with 5% $Na_2CO_3$ solution and with saturated NaCl solution. The resulting solution is evaporated to dryness and the residue is then chromatographed on silica, eluting with a toluene/EtOAc mixture (80/20; v/v). 0.52 g of the expected compound is obtained, m.p.=113° C.

NMR: 1.05 ppm: t: 3H; 1.25–1.65 ppm: m: 6H; 2.65 ppm: q: 2H; 2.80 ppm: m: 4H; 7.15 ppm: d: 2H; 7.50–7.80 ppm: m: 5H; 9.10 ppm: s: 1H.

EXAMPLE 2

N-Piperidino-5-(4-bromophenyl)-1-(2,4-dichlorophenyl)-4-ethylpyrazole-3-carboxamide A) 5-(4-Bromophenyl)-1-(2,4-dichlorophenyl)-4-ethylpyrazole-3-carboxylic Acid Chloride A mixture containing 97 g of thionyl chloride and 118 g of the compound of Preparation 4 in 1200 ml of toluene is prepared and is heated gradually to reflux and is then maintained at reflux for 3 hours. The reaction medium is concentrated.

B) N-Piperidino-5-(4-bromophenyl)-1-(2,4-dichlorophenyl)-4-ethylpyrazole-3-carboxamide The acid chloride formed is taken up in 380 ml of methylcyclohexane and 2.8 g of triethylamine in 218 ml of THF are introduced. The mixture is kept at 50° C.

A solution of 30 g of N-aminopiperidine and 28 g of triethylamine in 34 ml of methylcyclohexane is prepared and cooled to 10° C., and the mixture containing the acid chloride is added slowly. After stirring for 2 hours at 10° C., the product formed is filtered off, taken up in 2000 ml of DCM and washed twice with 2000 ml of water. The product is recrystallized from 4500 ml of methylcyclohexane and then filtered off and dried. 125 g of the expected compound are obtained.

What is claimed is:

1. A method for treating diseases involving the $CB_1$ cannabinoid receptors which comprises administering to a patient in need of such treatment an effective amount of N-piperidino-5-(4-bromophenyl)-1-(2,4-dichlorophenyl)-4-ethylpyrazole-3-carboxamide, of formula:

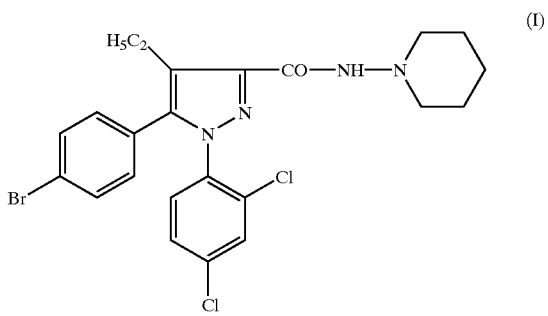

or a pharmaceutically acceptable salt and/or solvate thereof.

2. A method according to claim 1 for the treatment of psychotic disorders, for the treatment of appetite disorders and obesity, for the treatment of memory and cognitive disorders; for the treatment of alcohol dependency and for withdrawal from tobacco.

* * * * *